United States Patent [19]

Adler et al.

[11] 4,027,005

[45] May 31, 1977

[54] DIAGNOSTIC AGENTS

[75] Inventors: Norman Adler, Arlington; Leopoldo Lazaro Camin, Lexington, both of Mass.; Paul Gold, Hollis, N.H.

[73] Assignee: New England Nuclear Corporation, Boston, Mass.

[22] Filed: June 7, 1974

[21] Appl. No.: 477,069

[52] U.S. Cl. .............................. 424/1; 252/301.1 R; 424/1.5
[51] Int. Cl.[2] .................. A61K 29/00; A61K 43/00
[58] Field of Search .................... 424/1; 260/429 R; 23/230 B; 252/301.1 R; 250/303

[56] References Cited

UNITED STATES PATENTS

| 3,725,295 | 4/1973 | Eckelman et al. ........... 252/301.1 R |
| 3,749,556 | 7/1973 | Barak et al. ........................ 424/1 X |

*Primary Examiner*—Benjamin R. Padgett
*Assistant Examiner*—Christine M. Nucker
*Attorney, Agent, or Firm*—Sewall P. Bronstein; David G. Conlin

[57] ABSTRACT

Radionuclide diagnostic agents, comprising technetium-99m, a reducing agent, preferably a stannous reducing agent, and certain polyhydroxycarboxylic acids and derivatives thereof, i.e. glucoheptonic acid, lactobionic acid, galacturonic acid and glucuronic acid and salts thereof, are highly useful, both in the study and diagnosis of kidney morphology and function, and in the diagnosis of ischemic, infarcted or diseased tissue.

30 Claims, No Drawings

DIAGNOSTIC AGENTS

BACKGROUND

This invention pertains to agents which are useful in medicine as aids in detecting and diagnosing disease, in the examination and evaluation of body organs, and/or for other purposes, and to diagnostic and evaluatory processes using such agents. More particularly, it is concerned with certain radionuclide tracer agents which aid in radiological visualization of various types of tissues, including body organs, particularly the kidneys, and cysts, tumors or other diseased tissue, and/or dead or dying tissue.

The use of tracer compounds, which emit radiation from within the body, as medical tools has long been known. Early work included the use of such materials for testing liver function and biliary patency, and for the analysis of the physiological structure and function of the kidneys. A particularly important use of such agents is in the analysis of kidney morphology function and disorders, where radionuclides are used in a number of ways in order to get a number of different types of information.

In order to appreciate the various ways such agents can be used in connection with the kidneys, a brief and necessarily oversimplified description of kidney function is necessary. The bulk of the kidney consists of an outer portion called the cortex and an inner portion called the medulla. The cortex is reddish brown and contains approximately one million nephrons, the primary working unit of the kidney. The nephron consists of vessels and capillaries which carry the blood supply, a renal glomerulus, and a generally convoluted renal tubule. The renal glomerulus consists of capillary tuft having a few loops of capillary, which are almost completely encapsulated by an expansion of the renal tubule called Bowman's Capsule. The only parts of the glomerulus which are not covered by that capsule are the points at which a blood-supplying (afferent) vessel and a blood withdrawing (efferent) vessel enter and leave the capillary tuft. The renal tubule extends from a highly convoluted route proximal the capsule in the cortex, into the medulla, where it reverses itself in Henle's loop. The tubule returns to the cortex, where its distal portion follows a convoluted course until it empties into a collecting duct for the waste products. The collecting ducts lead to further kidney structures from which the urine leaves the body through the ureter, the bladder, and thence the urethra. The renal tubules are closely associated throughout their length with a close meshwork of capillaries, which carry an abundant blood supply.

Essentially three processes are involved in urine formation: filtration by the glomerulus, reabsorption of materials from the tubular fluid, primarily back into the blood stream, and secretion of materials into the tubular fluid.

The glomerulus functions as an ultrafilter, permitting particles smaller than the size of the pores in its walls to escape into the tubular fluid, thus filtering small colloidal and noncolloidal components of plasma. There is no selectivity to this filtration other than that of particle size, so the chemical composition and concentrations of materials in the filtrate are otherwise the same as those of plasma. The filtering process is directly related to the blood pressure. The effective filtering pressure is equal to the hydrostatic pressure in the glomerulus (normally about 75 to 80 mm Hg), minus the protein osmotic pressure (normally about 25 mm Hg), and minus the backpressure caused by resistance to movement to fluid in the tubule (normally about 7 mm Hg). Backpressure in the tubules is increased by increased intraureteral pressure, which is transmitted upward through the renal pelvis and inhibits the onward movement of tubular fluid. Pressure in the ureter rises if urine flow is impeded by obstruction of the ureteral openings into the bladder, or of the urethra.

While the total glomerulus filtration rate is very high, normally about 120 ml per minute (170 – 180 liters per day), the urine output is low, about 1 ml per minute (1½ liters per day). Thus as the filtrate passes through the tubules, it is changed in both volume and composition by the reabsorption of about 119 ml/minute of water and certain of its constituents. The cells of the tubule walls are responsible for the reabsorbing of materials to their approximate normal blood vessels. Much of the reabsorption is an "active" process, which involves so-called "carriers" within the tubular cell to aid in transporting the substance across the membrane. There is a limit to the rate at which such active transport systems can operate, and when this limit is reached, this material, e.g. glucose, which is present in excessive amounts in the filtrate, then fails to be reabsorbed and is excreted in the urine. In addition to active transport, passive transport occurs across the membrane through the processes of diffusion and osmosis. Secretion of materials by some of the cells in the tubular walls also plays an important part in renal function, some secretions merely being eliminated from the body, and other secretions being compounds which have specific functions in the renal system, such as controlling reabsorption of various materials.

More complex descriptions of the functions of the kidney are readily available, e.g. Smith, *The Kidney*, *Scientific American* 188:40 (1953), incorporated herein by reference.

The use of radionuclides in the diagnosis of kidney problems has been known for some time, the bulk of the work in this area having been done since the early or middle fifties. Such techniques can generally be divided into dynamic tests and static tests. The dynamic tests follow the course of radionuclides which have been injected into the blood as they are taken up and eliminated by the kidney. Such tests may merely monitor the radioactivity in the kidney over a period of time, or may consist of the taking of a number of rapid, sequential, short exposure radiophotographic images of the radioactivity in the kidney over a period of time, or may use one of a number of other similar techniques. Static tests comprise a number of techniques for obtaining images of the kidney containing the radionuclides, usually taken with longer exposure time, in order to optimize the visualization of the kidney morphology or structure.

For many years both types of renal investigation with radionuclides have enjoyed limited acceptance, largely because of the poor properties of the radionuclides used. Some, such as $^{131}$I-iodopyracet, did not allow adequate visualization of the kidneys, because of simultaneous accumulation in surrounding tissue, especially the liver. Some techniques utilized to avoid this problem produced undesirable side effects. Others, such as $^{131}$I-iodohippuran, were more kidney specific, and, being predominantly eliminated through active secretion by tubular cells as opposed to elimination by glomerular filtration, emphasized a different renal function than agents eliminated by filtration alone. However these agents were eliminated from the kidney so fast that rectilinear scanner images could only be obtained by giving a constant infusion of the agent, rather than a single dose. Alternate, longer lasting agents included the radioactive mercurials, but these are partially retained in the kidney for weeks or months after administration, resulting in continuing radiation exposure long after the scan is completed. Further, mercury scans were not as detailed in some respects as those using other agents, and mercurial agents were unable to attain high kidney/background contrast ratios rapidly. An excellent review of developments in this art is given in Blaufox et al., *Evaluation of Renal Function and Disease with Radionuclides* (S. Kanger AG, 1972), incorporated herein by reference.

The development of technetium-labelled agents has led to better visualization of the kidney morphology and more functional information, yet with far less radiation exposure. Such agents include combinations of technetium-99m with chelating agents, such as diethylenetramine pentaacetic acid (DTPA), or nitrilotriacetic acid (NTA), or more complicated combinations such as that offered under the trademark Renotec, by E. R. Squibb & Sons, Inc., which is a combination of ferric chloride, ascorbic acid and DTPA at higher pH. A more recent development has been the suggestion of agents consisting of radioactive technetium-gluconate complexes. See Boyd et al., $^{99}Tc^m$ *Gluconate Complexes for Renal Scintigraphy* Brit. J. Radiology, 46:604 (1973), incorporated herein by reference. While these agents were in many ways an improvement over those previous known, still some problems persisted, more particularly with regard to the uptake contrast ratios which enable the kidney to be distinguished from the surrounding tissues or organs, e.g. the liver, as well as the blood which fills the background.

Another development in radionuclide use, which is more recent than the use of the above agents in connection with the kidney, has been the attempt to find radionuclides which would enable detection, location and assessment of infarcts in various areas of the body. An infarct is a region of dead tissue caused by complete interference with the blood supply to that tissue usually is the result of occlusion of the supplying artery. Infarcts can occur in essentially any area of the body, the most serious including infarcts in the brain and infarcts in myocardium or heart muscle, caused by thrombi, embolisms, arterial sclerosis, etc. A number of attempts have been made to use radionuclides to confirm the presence of infarcts, and to give an assessment of their size and situs.

Radioactively-labelled compounds which are selectively incorporated into infarcted tissue have been used for such purposes. Such agents include chlormerodrin, radioactive mercury derivatives of fluorescein, and technetium-labelled tetracycline. See, Hubner, *Cardiovascular Research* 4:509 (1970) and Holman et al., *J. of Nuclear Medicine* 14: 95 (1973). The high uptake and long half life of the mercurial compounds, the difficulties encountered in their preparation, and interference by agent up-take in surrounding organs, e.g. the liver made the mercurial compounds unacceptable. Neighboring organ uptake was also a problem with tetracyline agent.

Accordingly, it is an object of the present invention to provide radionuclide agents that are highly suited as diagnostic agents, and as agents for the observation or study of the function of human or animal tissue. It is a further object to provide radionuclide agents which are suited for use in vivo, giving maximal information while at the same time exposing the body to minimal radiation dosage and discomfort. It is a further object to provide radionuclide agents for use in renal studies, which agents are highly kidney specific and are transferred to the kidney quickly with minimal accumulation in the surrounding organs, tissues or fluids. It is a further object to provide radionuclide agents for renal study which distinctly emphasize renal function differences. It is a further object to provide radionuclide agents for renal study which are highly suitable for both dynamic testing and static testing, being suitable to provide information concerning renal function, patency of excretory pathways, and renal morphology, in a single study. It is a further object to provide radionuclide agents for renal study which are eliminated by both glomerular filtration and tubular secretion, and give high kidney/background contrast ratios and permit high quality visualization of kidney morphology. It is a further object of the invention to provide radionuclide agents which are useful in detecting, locating and visualizing infarcted areas. It is a further object to provide radionuclide agents which are highly selectively incorporated or accumulated in ischemic, infarcted or diseased tissue. It is still a further object of this invention to provide radionuclide agents which are useable to advantage both in renal studies and in diagnosis of ischemic or diseased tissue and to methods of renal study and diagnosis which utilize such radionuclide agents.

Other objects and advantages will be apparent to those skilled in the art upon consideration of this disclosure or upon practice of the invention disclosed herein.

Briefly, it has now been discovered that combinations of radioactive materials with certain polyhydroxycarboxylic acids and derivatives thereof (hereafter referred to simply as "PHC compounds") have highly advantageous properties as compared with previously known radionuclide agents. More specifically, it has been found that combinations of technetium 99 with salts of glycoheptonic acid, lactobionic acid, galacturonic acid and glucuronic acid, give extremely effective radionuclide agents. Moreover, it has surprisingly been found that such agents are useful not only in renal study but also in diagnosis of ischemic, infarcted or diseased areas.

The radionuclide agents of the present invention are kidney specific diagnostic agents which make it possible to identify a variety of renal disorders and to obtain in a single investigation information which had previously required a plurality of different investigations. Unlike the mercurial agents, the short effective half life of these technetium agents minimize any danger from overexposure to radiation. On the otherhand, the period of retention of usable levels of the technetium agents of this invention in the kidney is larger than the period of retention for example of radioactive iodohippuran, and thus allows greatly improved static images of the kidney to be made long after administration which would be practically impossible with iodohippuran. The agents of the instant invention are more kidney specific and give higher kidney/background contrast ratios than those agents previously known, even the known technetium stannous gluconate complexes.

Further, the same agents are useful not only in renal studies, but also in the location and identification of ischemic, infarcted or diseased areas in the body, by radionuclide tracing or imaging techniques, applied for example to the heart or the brain. Suitable techniques are known to the art, and are disclosed for example in Hubner, supra, in Holman, supra, in *Physician's Desk Reference for Radiology and Nuclear Medicine* (Medical Economics Co., 1973) and in *Handbook of Radioactive Nuclides* (Chemical Rubber Co., 1969).

The agents of the present invention are produced by binding technetium-99m to the above PHC compounds either by using chemical reducing agents, or electrolytically, both methods of binding being known per se in the art.

Where the binding is by chemical reducing agent, the PHC compound is preferably mixed with a reducing agent, e.g. stannous ions, and pertechnetate is thereafter added to that mixture. While not wishing to be bound by theory, it is believed that the pertechnetate is reduced by the stannous ions and reacted with the PHC compound to form the radionuclide agents of the present invention, which is believed to be some type of technetium-stannous-carbohydrate acid complex. The PHC compound may be any salt of glucoheptonic acid, lactobionic acid, galacturonic acid or glucuronic acid which is soluble in the mixing medium. Preferably the components are mixed in aqueous medium and the PHC compound is a soluble alkali or alkaline earth metal salt. However, other pharmacologically acceptable media can be used. Preferably the reducing agent is also soluble in the mixing medium, with water soluble sources of stannous ions, such as stannous chloride, or of ferrous ions, such as ferrous ascorbate being preferred. Stannous ions constitute the most preferred reducing agent. Other suitable reducing agents will be apparent to those skilled in the art.

The source of technetium should also preferably be water soluble, with preferred sources being alkali and alkaline earth metal pertechnetates. The technetium is preferably obtained in the form of fresh sodium pertechnetate from a sterile NEN $^{99m}$Tc Generator. Any other source of pharmacologically acceptable $^{99m}$Tc can be used, and a number of $^{99m}$Tc generators are available.

The maximum amount of reducing agent which can be used is the amount beyond which precipitation of the reducing agent occurs, and the minimum amount required is that amount necessary to bind a sufficient amount of $^{99m}$Tc to the carbohydrate acid to achieve significant selective tissue or organ uptake. These amounts can be readily determined for particular technetium-reducing agent - carbohydrate acid mixtures by routine experimentation. Very small amounts of reducing agent are effective for this purpose, but because such agents are usually easily oxidized, compositions using extremely small amounts are likely to loose this effectiveness over a period of time after handling or during use. Thus as a minimum, the amount of reducing agent used should be sufficient to supply 0.1 micrograms of reducing agent per milliliter of the diagnostic agent to be injected. As the amount of reducing agent is increased, there appears to be a point for any given combination of particular reducing agent and PHC compound, beyond which binding effectiveness no longer increases, and in fact may decrease, upon further additive of reducing agent. Some level of binding effectiveness appears to be achieved for even very high levels of reducing agent. Advantage can sometimes be taken of the natural attrition of reducing through oxidation during handling or storage, by providing compositions containing more than the optimum amount of reducing agent, which in effect will be reduced to the optimum amount by that attrition prior to use. In the presently preferred technetium-99m-stannous-glucoheptonate system, the amount of stannous reducing agent is between about 1 and 100 micrograms, preferably between 5 or 10 and 40 micrograms per milliliter of the diagnostic agent to be injected.

It also appears important that the PHC compound be in large excess of the reducing agent. Preferably the reducing agent should be present in an amount of about 0.0005% to 0.5%, more preferably 0.005% to 0.1% of the PHC compound.

Sufficient technetium-99m should be present to give easy detection in the body. The amount necessary appears, to depend essentially completely on the level of radioactivity desired, since if the proper amounts and ratios of reducing agent and PHC compound are present, as much as 90 to 95% or greater of the technetium-99m is bound to the PHC compound.

In the presently preferred system, a sterile, non pyrogenic lyophilized mixture of about 0.1 mg. of stannous chloride dihydrate reducing agent and about 200 mg. of sodium glucoheptonate is provided in a sterile vial, which is preferably mixed with 3 to 7 ml of the output of a NEN $^{99m}$Tc Generator, shortly before use.

While binding of the technetium-99m through use of a chemical reducing agent is presently preferred, it may also be done electrolytically, using at least one electrode which comprises an oxidizable material such as iron, tin, zirconium, or the like. Such binding methods are known in the art, as disclosed, for example, by Boyd et al., supra.

The diagnostic compositions of the invention may also contain additional pharmacologically acceptable ingredients which do not interfere with their diagnostic functions. For example, the eluate obtained from standard $^{99m}$Tc generators may contain saline salts, or saline solutions may be used to dilute highly radioactive diagnostic compositions to the proper level for administration.

The pH of the agents should be adjusted if necessary by pharmacologically acceptable acids or bases, so that the pH of the agent is from about 3 to 10, preferably about 5 to 8.

Aseptic techniques and sterile non-pyrogenic ingredients should be used at all steps, such procedures being standard to those skilled in the art.

In order to prevent oxidation of the stannous ions other than in formation of the complex, care should be taken to exclude all oxidizing agents from the radionuclide agent and the starting materials. For this reason, sources of technetium-99m containing significant amounts of oxidants should not be used. Oxygen should also be excluded, as by purging the various containers used in preparation and storage with an inert gas, e.g. nitrogen, for a sufficient length of time. However, it is not essential (but highly preferred) to use a nitrogen flushed system.

After mixing, the solution containing the reducing agent and the PHC compound can be sterilized if necessary by standard procedures, as by passing them through a Millipore biological filter of about 0.22 micron pore size under a nitrogen atmosphere. Thereafter milliliter portions of the sterile solutions are poured into individual sterile and non-pyrongenic storage glass vials under a nitrogen atmosphere.

As indicated above, the individual portions are preferably lyophilized by conventional freeze drying techniques under aseptic conditions to remove the water. This provides a solid stannous-PHC complex or mixture of some sort, which aids in shipping and storage and is more stable than the complex in solution. The vials can be sealed and stored until needed to form the fresh $^{99m}$Tc-stannous-PHC agent at the use situs.

While it is preferred that the stannous chloride and the PHC compound be mixed together prior to admixture with the technetium, the order of admixture can also be technetium plus PHC compound followed by admixture of stannous chloride, or even stannous chloride plus technetium followed by addition of PHC compound.

The technetium 99m-stannous-PHC (e.g. glucoheptonate) complex or mixture is aseptically intravenously injected into the blood stream. The preferred dosages are between about 1 and 20 or 25 millicuries, preferably between about 10 and 15 mCi of $^{99m}$Tc-Stannous Glucoheptonate for the normal 70 kg patient. Higher and lower amounts may be used in certain circumstances although greater dosages increase patient radiation exposure. Lower amounts may be desirable for example when simpler tests such as blood clearance rate tests are run. The study may be commenced immediately after administration either by sequential visualization devices such as scintillation cameras, or by the probes conventionally used in producing a renogram. Static imagery is optionally performed 1 hour or more after injection. Distribution data in rats concerning the glucoheptonate agent indicates that about 15 – 25% of the injected dose is taken up by the kidneys within one hour post injection, with the total blood activity rapidly clearing to less than 2% within the same time period. Data for humans indicates that about 25% of the injected dose is excreted in the urine within the first hour after injection. The study may be conducted with a conventional gamma-ray-excited scintillation device or camera or rectilinear scanners, or external probes having the capability of detecting gamma rays of the energy released by $^{99m}$Tc.

Standard percautions for use of radioactive materials should be observed in handling those solutions containing $^{99m}$Tc.

The acute toxicity level in mice ($LD_{50}$) for stannous glucoheptonate administered intravenously in about 1500 mg/kg. Sub-acute toxicity studies in mice at levels of 800, 400 and 80 mg/kg per day for 15 days have shown no ill effects. Similarly no untoward effects were noted in sub-acute toxicity studies in dogs at a level of 19 mg/kg per day for 14 days.

The invention will be further clarified with reference to the following illustrative embodiments, which are intended to be purely exemplary and not to be construed in any limiting sense.

EXAMPLES 1 – 8

Technetium-99m-stannous-PHC agents are prepared as follows. First, a mixture containing about 0.1 mg. of stannous chloride dihydrate with 200 mg. of the sodium salt of various PHC compounds per milliliter of water is prepared. In Example 1, the salt is sodium glucoheptonate. In Example 2, that salt is sodium lactobionate. In Example 3m that salt is sodium galacturonate. In Example 4, that salt is sodium glucuronate. In Example 5, the salt is sodium gluconate. The resulting mixtures are lyophilized using standard freeze drying equipment, and in each case the resulting solid is mixed with 3 – 7 ml of the eluate of a sterile NEN $^{99m}$TC Generator, which eluate also contains 0.9% saline salt. The amount of eluate added to the solid is determined by the dosage required and the activity of the eluate at the time of addition. After thoroughly dispersing and dissolving the lyophilized solid, the radionuclide agents are ready for injection.

Example 6 concerns the use of a commercially available renal imaging agent, Renotec, obtained as a kit from E. R. Squibb & Sons, Inc., of Princeton, New Jersey. The kit comprises a vial and two disposable syringes. The vial contains about 2 ml of an aqueous solution reportedly consisting of about 10 mg. ferric chloride, 5–10 mg. of acorbic acid and sodium hydroxide to adjust pH to 2.0–4.0. One syringe contains 2 ml of a sterile 0.07 N sodium hydroxide solution, and the other syringe contains 2 ml of a sterile diethylenetriamine pentaacetic acid (DTPA) solution, containing about 5 mg. of DTPA. The radionuclide agent was prepared in accordance with instructions supplied with the kit. Briefly, 1 to 5 ml of $^{99m}$TC eluate, again depending on the dosages and activity at time of preparation, were mixed with the contents of the vial. The contents of the sodium hydroxide syringe were then injected and mixed in the vial, and then the contents of the DTPA syringe were injected and mixed with the vial contents. The Renotec scanning agent was then ready for injection.

Example 7 concerns the use of a technetium-99m-stannous-DTPA agent similar to those known to the art. A mixture containing about 0.25 mg. of stannous chloride dihydrate and about 5 mg. of the calcium trisodium salt of DTPA per milliliter of water is prepared, and one ml amounts are dispersed in individual vials and lyophilized using standard freeze-drying procedures. The agent results from dissolving the lyophilized mixture in 3–7 ml of the $^{99m}$Tc eluate.

Example 8 concerns the use of a nitrilotriacetic acid radionuclide agent similar to those previously known. A mixture containing about 50 micrograms of stannous chloride dihydrate is prepared. One milliliter portions are dispersed in vials, and lyophilized using standard freeze-drying techniques. The lyophilized mixture is dissolved in 3–7 ml of the standard $^{99m}$Tc eluate, and is ready for use.

Each of the foregoing renal scanning agents is aseptically intravenously injected (0.25 ml containing about 3–5 mCi) into adult rats. One hour later the rats are sacrificed, and the blood collected, weighed and counted. The organs of interest, e.g. the kidney, the liver, and the gastrointestinal tract, are individually weighed and the radioactivity contained therein counted. The amount of radioactivity injected is determined by counting the radioactivity in the syringe before and after injection. The organ distribution values are reported as the percent of the activity injected which is observed in the organ, corrected for the radioactive decay of technetium. The organ uptake contrast ratios are determined by determining the relative activity contained per gram of the organs compared. Thus for example the kidney/liver organ uptake contrast ratio is equal to the radioactivity found in the kidney divided by the weight of the kidney, all divided by the radioactivity per gram in the liver. The results are reported in Table I below. Each value represents the average of observations on at least two animals, and while there is some variation between individual animals the results reported are representative for the radionuclide agent tested.

TABLE I

Comparative One Hour Rat Organ Distribution of Agents Prepared With $^{99m}Tc$ $O^-_{\;4}$ and $Sn^{++}$

| Example Nos. | 1 | 2 | 3 | 4 | 5 | 6 | 7 | 8 |
|---|---|---|---|---|---|---|---|---|
| | Glucoheptonic Acid | Lactobionic Acid | Galacturonic Acid | Glucuronic Acid | Gluconic Acid | RENOTEC[R] | DTPA[a] | NTA[b] |
| Kidney | 18 | 23 | 21 | 10 | 16 | 15 | 5.0 | 10 |
| G.I. | 5.0 | 6.2 | 5.8 | 5.5 | 4.8 | 12.5 | 1.1 | 2.8 |
| Liver | 0.7 | 1.3 | 0.9 | 0.8 | 1.4 | 2.7 | 0.3 | 1.3 |
| Blood | 1.1 | 1.8 | 1.1 | 1.5 | 2.3 | 3.8 | 1.0 | 6.6 |
| Organ Uptake Contrast Ratios | | | | | | | | |
| Kidney/blood | 105 | 82 | 128 | 91 | 40 | 22 | 32 | 66 |
| Kidney/liver | 115 | 102 | 118 | 115 | 50 | 27 | 77 | 25 |
| Kidney/G.I. | 44 | 57 | 41 | 39 | 55 | 12 | 65 | 32 |

[R] Squibb
[a] Diethylene Triamine Pentaacetic Acid
[b] Nitrilotriacetic acid

As can be seen, the kidney/blood organ uptake contrast ratios for the compositions of this invention vary between 82 and 105, while those for the corresponding gluconic acid complex (40), the commercial agent Renotec (22) and the chelating agent complexes DTPA (22) and NTA (6) are quite low, all being less than half of that obtained by the agents of the invention. The ratio is a measure of the ability to accurately distinguish radioactivity emanating from the kidney as against a blood filled background. Striking improvements are also observed in the kidney/liver contrast ratio, which is a measure of the ability to radiographically distinguish the kidney from the liver, a well known problem with previous agents. Generally the kidney/gastrointestinal contrast rations are of about the same order of magnitude as the better of the prior agents.

This difference in ability to accurately define the kidney against the neighboring organs is quite surprising, especially in view of the closeness in structure between, for example, the glucoheptonic acid agent and previously known glyconic acid agents. No solid reasons for these observed differences are presently known.

EXAMPLES 9 and 10

The technetium-99m-stannous-glucoheptonate agent of Example 1, supra is compared with a technetium-99m-stannous-tetracycline agent, see Holman et al, supra, for effectiveness in preferentially accumulating in infarcted, rather than normal, myocardial tissue. In each case a myocardial infarct is produced in adult rats by surgery. In Example 9, doses of about 3–5 mCi each of the glucoheptonate and tetracycline agents respectively are injected 3 hours after infarct was induced. The animals are sacrificed 1 hour after injection and the heart removed. The infarcted tissue, which is visibly distinguishable from normal myocardial tissue, was excised, weighed and counted. The normal myocardial tissue was also weighed and its activity counted and the results are reported as the ratio of the activity per gram of the infarcted tissue to the activity per gram of the normal tissue (A), and the ratio of the activity per gram of the infarcted tissue to activity per gram in the blood (B). Example 10 reports similar results, the difference being that in that example the radionuclides were injected into the live rats eighteen hours after the infarct was induced, rather than three hours. Examples 9 and 10 are reported in Table II below:

Table II

| Agent | Infarction Tests | Example 9 | Example 10 |
|---|---|---|---|
| Glucoheptonate complex | A | 10.3 | 6.7 |
| | B | 4.5 | 3.2 |
| Tetracycline complex | A | 5.9 | 3.7 |
| | B | 2.5 | 2.0 |

The results of Examples 9 and 10 both indicate that the glycoheptonate agent of the present invention was more effective in preferentially accumulating in infarcted, rather than normal, tissue than the tetracycline infarct agent.

While particular embodiments of the present invention have been described herein, they are intended to be exemplary only, with the true scope and spirit of the invention being indicated in the specification and the following claims:

We claim:

1. A radioactive diagnostic composition, comprising a product of admixture of technetium-99m, a reducing agent, and salt of a polyhydroxycarboxylic acid selected from the group of glucoheptonic acid, lactobionic acid, galacturonic acid and glucuronic acid.

2. The composition of claim 1, wherein said reducing agent comprises a stannous reducing agent.

3. The composition of claim 2, wherein the stannous reducing agent is present in an amount of at least 0.1 microgram per milliliter of composition.

4. The composition of claim 3, wherein the stannous reducing agent is present in an amount of from about 1 to 100 micrograms per milliliter of composition.

5. The composition of claim 3, wherein the stannous reducing agent is present in an amount of from 10 to 40 micrograms per milliliter of composition.

6. The composition of claim 3, wherein the stannous reducing agent is present in an amount of from 0.0005% to 0.5% by weight of the polyhydroxycarboxylic acid salt.

7. The composition of claim 3 wherein the stannous reducing agent is present in an amount of from 0.005% to 0.1% by weight of the polyhydroxycarboxylic acid salt.

8. The composition of claim 7, wherein the polyhydroxycarboxylic acid salt is an alkali or alkaline earth metal salt of glucoheptonic acid.

9. The composition of claim 7, further comprising a pharmacologically acceptable carrier.

10. A composition suitable for the preparation of a radioactive diagnostic agent, comprising a mixture of a reducing agent and salt of a polyhydroxycarboxylic acid selected from the group of glucoheptonic acid, lactobionic acid, galacturonic acid and glucuronic acid.

11. The composition of claim 10, wherein said reducing agent is a stannous reducing agent.

12. The composition of claim 11, wherein said stannous reducing agent is present in amount of from .005% to 0.1% by weight of said polyhydroxycarboxylic acid salt.

13. The composition of claim 11, wherein said mixture is a solid.

14. A kit for forming a radioactive diagnostic composition comprising a reducing agent and a polyhydroxycarboxylic acid selected from the glucoheptonic acid, lactobionic acid, galacturonic acid and glucuronic acid, packaged in a sealed, sterile, non-pyrogenic container.

15. The kit of claim 14, wherein said mixture is a freeze dried solid.

16. The kit of claim 15, wherein said polyhydroxycarboxylic acid comprises glucoheptonic acid.

17. A method of concentrating $^{99m}Tc$ in vivo in a kidney of a mammal comprising intravenously administering to the animal a radioactive composition comprising a product of admixture of technetium-99m, a reducing agent, and a salt of a polyhydroxycarboxylic acid selected from the group of glucoheptonic acid, lactobionic acid, galacturonic acid and glucuronic acid.

18. The method of claim 17, wherein said composition contains sufficient technetium-99m to give radioactivity in the amount of from about 1 to 25 mCi per 75 kilograms of body weight.

19. The method of claim 17, wherein said composition contains sufficient technetium-99m to give radioactivity in the amount of from about 10 to 15 mCi per 75 kilograms of body weight.

20. The method of claim 17, wherein said reducing agent comprises a stannous reducing agent, and is present in an amount of at least 0.1 micrograms per milliliter of said mixture.

21. The method of claim 20, wherein said reducing agent is a stannous reducing agent, and is present in an amount of from about 0.0005 to 0.5% by weight of the polyhydroxycarboxylic acid.

22. The method of claim 21, wherein the polyhydroxycarboxylic acid is glycoheptonic acid.

23. A method of concentrating technetium-99m in ischemic infarcted or diseased tissue in an animal comprising intravenously administering to the animal a radioactive composition comprising a product of admixture of technetium-99m, a stannous reducing agent, and a polyhydroxycarboxylic acid selected from the group of glucoheptonic acid, lactobionic acid, galacturonic acid and glucuronic acid, said stannous reducing agent being present in an amount of from .01 to .1% by weight of said polyhydroxycarboxylic acid.

24. A method of preparing a radioactive diagnostic agent, comprising forming a mixture of a reducing agent and a salt of a polyhydroxycarboxylic acid selected from the group of glucoheptonic acid, lactobionic acid, galacturonic acid and glucuronic acid, and combining technetium-99m with said mixture.

25. The method of claim 24, wherein said mixture is lyophilized prior to being combined with technetium-99m.

26. A radioactive diagnostic composition, comprising a product of admixture of technetium-99m, a reducing agent selected from the group of stannous ions and ferrous ions, and a salt of a polyhydroxycarboxylic acid selected from the group of glucoheptonic acid, lactobionic acid, galacturonic acid and glucuronic acid, said reducing agent being present in an amount of from about 1 to 100 micrograms per milliliter of composition, the amount of said reducing agent being from about 0.0005 to 0.5% of said polyhydroxycarboxylic acid, and said technetium-99m being present in an amount sufficient to provide radioactivity in the amount of from about 1 to 25 mCi.

27. A radioactive diagnostic composition comprising technetium-99m bound to a salt of a polyhydroxycarboxylic acid selected from the group of glucoheptonic acid, lactobionic acid, galacturonic acid and glucuronic acid.

28. The composition of claim 27, wherein the polyhydroxycarboxylic acid salt is an alkali or alkaline earth metal salt of glucoheptonic acid.

29. A method of preparing a radioactive diagnostic agent, comprising forming a mixture of technetium-99m and a polyhydroxycarboxylic acid selected from the group of glucoheptonic acid, lactobionic acid, galacturonic acid and glucuronic acid, and subjecting said mixture to electrolysis in the presence of an oxidizable electrode.

30. The method of claim 29, wherein the oxidizable electrode comprise a metal selected from the group of iron, tin and zirconium.

* * * * *

UNITED STATES PATENT OFFICE
CERTIFICATE OF CORRECTION

PATENT NO. : 4,027,005
DATED : May 31, 1977
INVENTOR(S) : Norman Adler, Leopoldo Camin and Paul Gold It is certified that error appears in the above-identified patent and that said Letters Patent are hereby corrected as shown below:

Column 2, line 55, "time" should be ---times---
Column 7, line 5, delete "the"
Column 7, line 45, "percautions" should be ---precautions---

Column 9, line 43, "glyconic" should be ---gluconic---
Column 10, line 32, "glycoheptonate" should be ---glucoheptonate ---
Claim 22, line 50 Column 11, "glycoheptonic" should be ---glucoheptonic---
Claim 30, column 12, line 49 "comprise" should be ---comprises--

Signed and Sealed this

Twentieth Day of December 1977

[SEAL]

Attest:

RUTH C. MASON
*Attesting Officer*

LUTRELLE F. PARKER
*Acting Commissioner of Patents and Trademarks*